US009005601B2

(12) United States Patent
Hargis et al.

(10) Patent No.: US 9,005,601 B2
(45) Date of Patent: Apr. 14, 2015

(54) METHODS AND COMPOSITIONS INCLUDING SPORE-FORMING BACTERIA FOR INCREASING THE HEALTH OF ANIMALS

(75) Inventors: Billy Hargis, Fayetteville, AR (US);
Ross Wolfenden, Pea Ridge, AR (US);
Neil R. Pumford, Bentonville, AR (US);
Marion Morgan, Springdale, AR (US);
Anita Menconi, Fayetteville, AR (US);
Guillermo Tellez, Fayetteville, AR (US);
Amanda Wolfenden, Pea Ridge, AR (US); Srichaitanya Shivaramaiah, Kitchener (CA)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 13/810,549

(22) PCT Filed: Jul. 18, 2011

(86) PCT No.: PCT/US2011/044326
§ 371 (c)(1),
(2), (4) Date: Feb. 6, 2013

(87) PCT Pub. No.: WO2012/009712
PCT Pub. Date: Jan. 19, 2012

(65) Prior Publication Data
US 2013/0136695 A1    May 30, 2013

Related U.S. Application Data

(60) Provisional application No. 61/365,188, filed on Jul. 16, 2010.

(51) Int. Cl.
*A61K 35/74* (2006.01)
*C12N 1/20* (2006.01)
*A23K 1/00* (2006.01)
*A23K 1/18* (2006.01)
*A23L 1/30* (2006.01)

(52) U.S. Cl.
CPC . *C12N 1/20* (2013.01); *A23K 1/002* (2013.01); *A23K 1/009* (2013.01); *A23K 1/1826* (2013.01); *A23L 1/3014* (2013.01); *A61K 35/742* (2013.01)

(58) Field of Classification Search
None
See application file for complete search history.

(56) References Cited

U.S. PATENT DOCUMENTS

| 4,335,107 A | 6/1982 | Snoeyenbos et al. |
| 4,657,762 A | 4/1987 | Mikkola et al. |
| 4,689,226 A | 8/1987 | Nurmi et al. |
| 5,401,501 A | 3/1995 | Pratt |
| 5,451,400 A | 9/1995 | Stern et al. |
| 5,612,055 A | 3/1997 | Bedford et al. |
| 5,807,546 A | 9/1998 | Stern et al. |
| 6,017,525 A | 1/2000 | Logan et al. |
| 6,110,455 A | 8/2000 | Hargis et al. |
| 6,214,335 B1 | 4/2001 | Stern et al. |
| 6,461,607 B1 | 10/2002 | Farmer |
| 7,247,299 B2 | 7/2007 | Lin et al. |
| 7,700,094 B1 | 4/2010 | Nsereko et al. |
| 7,708,988 B2 | 5/2010 | Farmer |
| 7,754,469 B2 | 7/2010 | Baltzley et al. |
| 2001/0018048 A1 | 8/2001 | Leer et al. |
| 2002/0146399 A1 | 10/2002 | Raczek |
| 2003/0031659 A1 | 2/2003 | Farmer |
| 2004/0101525 A1 | 5/2004 | Lin et al. |
| 2004/0241150 A1 | 12/2004 | Hargis et al. |
| 2005/0084500 A1 | 4/2005 | Molly et al. |
| 2005/0271643 A1 | 12/2005 | Sorokulova et al. |
| 2006/0099197 A1 | 5/2006 | Farmer |
| 2008/0044501 A1 | 2/2008 | Lee et al. |
| 2008/0057047 A1 | 3/2008 | Sas et al. |
| 2008/0171102 A1 | 7/2008 | Rehberger et al. |
| 2008/0233104 A1 | 9/2008 | Farmer |
| 2009/0257995 A1 | 10/2009 | Mochizuki |
| 2010/0074873 A1 | 3/2010 | Watson |
| 2010/0074994 A1 | 3/2010 | Harel et al. |
| 2010/0092428 A1 | 4/2010 | Schmidt et al. |
| 2010/0143417 A1 | 6/2010 | James et al. |
| 2012/0225050 A1 | 9/2012 | Knight et al. |

FOREIGN PATENT DOCUMENTS

| CN | 101569375 A | 11/2009 |
| CN | 101580799 A | 11/2009 |
| EP | 2 011 858 A1 | 1/2009 |
| RU | 2 203 947 C1 | 5/2003 |

(Continued)

OTHER PUBLICATIONS

Wolfenden, Evaluation of Selected Antibiotic Alternatives for Control of Enteric Bacterial Pathogens of Commercial Poultry, Dissertation, Univ. Arkansas, May 2010.*
Zhu et al. (Food Control, 19:654-661, 2008).*
Abdollahi, M.R. et al., "Effect of different levels of bacterial probiotic on broilers performance," Animal Science Department, College of Agiculture, University of Tehran, Karaj-Iran.
Alexopoulos, C. et al., "Field evaluation of the effect of a probiotic-containing *Bacillus licheniformis* and *Bacillus subtilis* spores on the health status, performance, and carcass quality of grower and finisher pigs," (2004) Journal of Veterinary Medicine Series A Physiol Pathol Clin Med 51(6):306-312.

(Continued)

*Primary Examiner* — Brian J Gangle
(74) *Attorney, Agent, or Firm* — Snell & Wilmer LLP

(57) ABSTRACT

Methods, compositions and bacterial isolates for improving the gastrointestinal health of animals and in particular of poultry are provided herein. The methods include administering an endospore-forming bacteria to an animal. The bacteria are selected for the ability to reduce the growth and presence of bacterial pathogens, such as *Salmonella*, *Clostridium*, and *Campylobacter*, in the gastrointestinal tract of the animal. The bacteria are also selected for the ability to improve at least one production parameter in the animal.

19 Claims, 2 Drawing Sheets

(56) References Cited

FOREIGN PATENT DOCUMENTS

| WO | WO 88/06619 | 9/1988 |
|---|---|---|
| WO | WO 2004/044186 | 5/2004 |
| WO | 2004080200 A1 | 9/2004 |
| WO | WO 2005/019417 | 3/2005 |
| WO | WO 2010/068231 | 6/2010 |
| WO | WO 2012/009712 | 1/2012 |
| WO | WO 2012/044984 | 4/2012 |
| WO | 2014022572 A1 | 2/2014 |

OTHER PUBLICATIONS

Alexopoulos, C. et al., "Field evaluation of the, efficacy of a probiotic containing *Bacillus licheniformis* and *Bacillus subtilis* spores, on the health status and performance of sows and their litters," (2004) Journal of Animal Physiology and Animal Nutrition 88(11-12):381-392 (Abstact).

Corcionivoschi, N. et al., "The effect of probiotics on animal health," (2010) Scientific Papers: Animal Science and Biotechnologies 43(1):35-41.

Hong, H.A. et al. "The use of bacterial spore formers as probiotics," (2005) FEMS Microbial Rev 29(4):813-835 Epub Dec. 16, 2004.

Kowalski, Z.M. et al., "Performance of Holstein calves fed milk-replacer and starter mixture supplemented with probiotic feed additive," (2009) Journal of Animal and Feed Sciences 18:399-411.

Kritas, S.K. et al., "Effect of *Bacillus licheniformis* and *Bacillus subtilis* supplementation of ewe's feed on sheep milk production and young lamb mortality," (2006) Journal of Veterniriary Medicine Series A Physiol Pathol Clin Med 53(4):170-173.

Link, R. et al., "Composition of sow's milk and selected metabolic indices after administration of probiotics," (2007) Research in Pig Breeding 1(1):40-42.

Mahdavi, A.H. et al., "Effect of probiotic supplements on egg quality and laying hen's performance," (2005) International Journal of Poultry Science 4(7):448-492.

Mahdavi, A.H. et al., "Effect of probiotic inclusion in different levels of barley substitution for corn diets on egg quality and laying hen's performance," (2005) Pakistani Journal of Biological Sciences 8(11):1521-1528.

Mutus, R. et al., "The effect of dietary probiotic supplementation on tibial bone characteristics and strength in broilers," (2006) Poultry Science 85(9):1621-1625.

Pelicano, E.R.L. et al., "Effect of different probiotics on broiler carcass and meat quality," (2003) Brazilian Journal of Poultry Science 5(3)207-214.

Sabatkova, J. et al, "The probiotic BioPhts 2B as an alternative to antibiotics in diets for broiler chickens," (2008) ACTA VET, BRNO 77:569-574.

Wolfenden, R.E., Evaluation of selected antibiotic alternatives for control of enteric bacterial pathogens of commercial poultry, (2010) ProQuest Dissertation & Theses: The Sciences and Engineering Collection.

Wolfenden, R.E., Evaluation of a screening and selection method for *Bacillus isolates* for use as effective direct-fed microbials in commercial poultry, (2010) International Journal of Poultry Science 9(4):317-323.

International Search Report and Written Opinion for International Patent Application No. PCT/US2011/044326 dated Mar. 14, 2012 (10 pages).

International Search Report and Written Opinion issued in International Application No. PCT/US2013/053047 on Jul. 31, 2013.

Extended European Search Report issued in European Application No. 11807617.3 on Mar. 6, 2014.

Stringfellow, K., et al., "Evaluation of Probiotic Administration on the Immune Response of Coccidiosis-Vaccinated Broilers," (2011) Poultry Science , vol. 90, pp. 1652-1658.

* cited by examiner

Figure 1. *In vitro* Testing and Isolation of Candidate Isolates
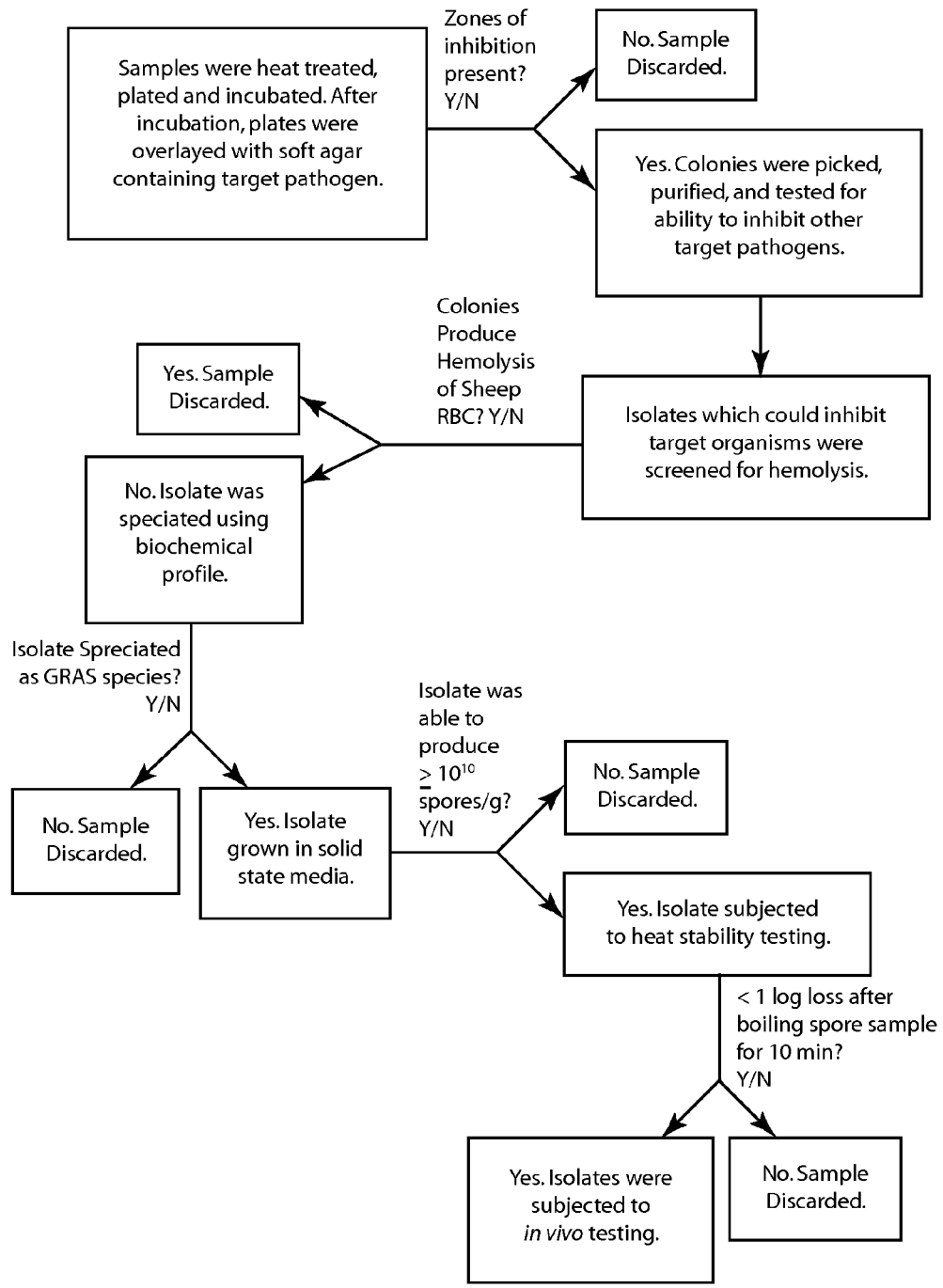

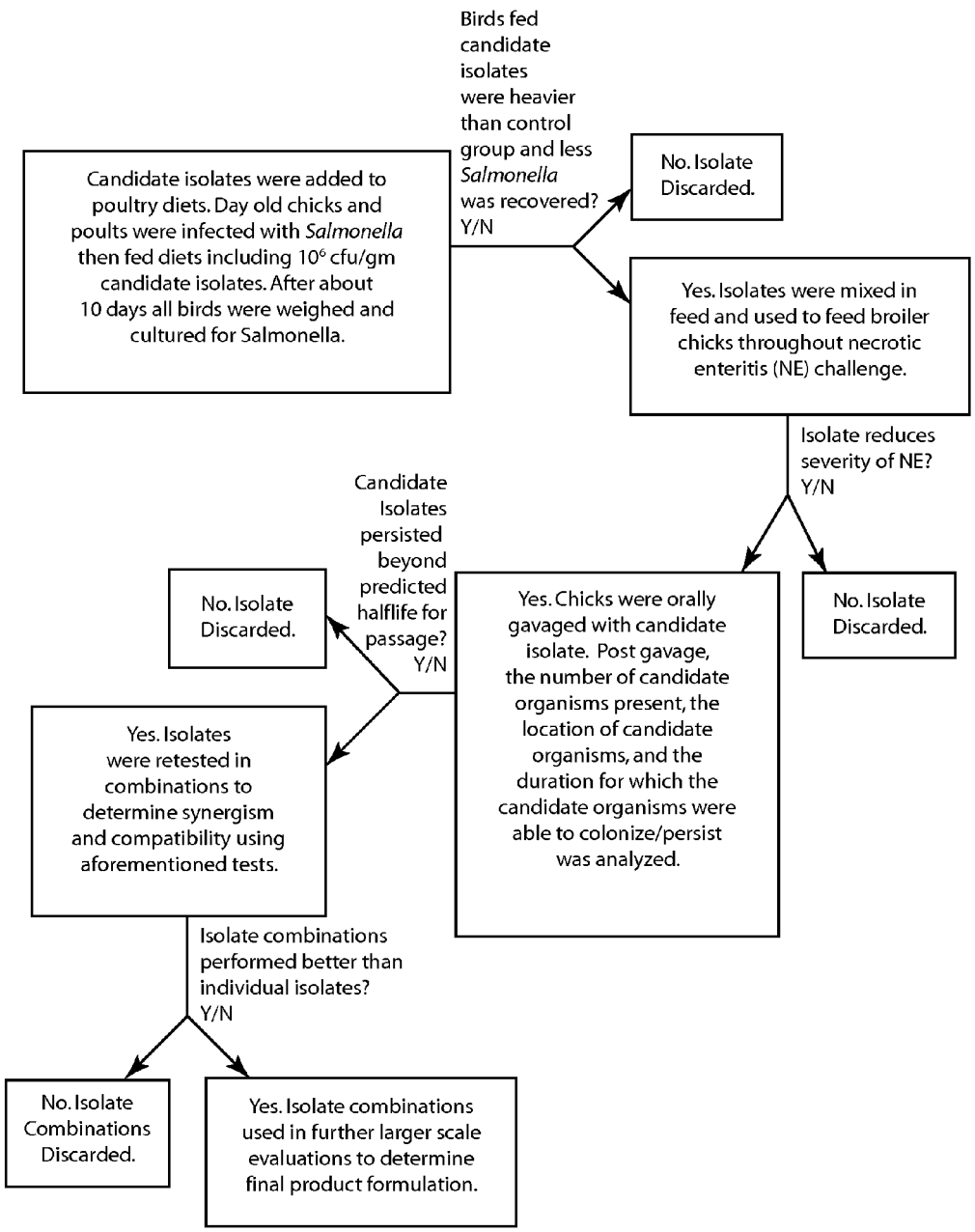
Figure 2. *In vivo* Testing of Candidate Isolates

METHODS AND COMPOSITIONS INCLUDING SPORE-FORMING BACTERIA FOR INCREASING THE HEALTH OF ANIMALS

CROSS-REFERENCE TO RELATED APPLICATIONS

This patent application claims the benefit of priority of U.S. Provisional Patent Application No. 61/365,188, filed Jul. 16, 2010, which is incorporated herein by reference in entirety.

STATEMENT REGARDING FEDERALLY SPONSORED RESEARCH

This invention was made with United States government support awarded by the United States Department of Agriculture Food Safety Consortium grant number 2010-34211-20961. The United States may have certain rights in this invention.

FIELD OF THE INVENTION

The present invention relates in general to methods for improving the health of agricultural animals. In particular, the present invention relates to bacterial isolates, probiotic formulations comprising the isolates and methods selecting and of using the probiotic formulations and isolates to improve the health of poultry.

BACKGROUND OF THE INVENTION

The use of antibiotics in animal agriculture, in particular poultry production, is coming under increasing pressure from both consumers and government regulatory agencies. This has created a need for effective antibiotic alternatives. The use of effective probiotics or direct-fed microbials (DFM) in animal agriculture may be one such potential alternative. Presently there are two general subsets of bacteria used in probiotic or DFM applications: lactic acid bacteria and *Bacillus* spp.

While some isolates are proven effective, lactic acid bacteria have the disadvantage that they must be applied through the drinking water. This is because these types of organisms are generally not tolerant of the heat needed to pellet many animal feed diets. Additionally, since these products must be applied through the water, the individual farmer is responsible for applying the product. This often leads to issues of compliance with proper administration guidelines leading to improper application and reduced efficacy of these products.

SUMMARY OF THE INVENTION

Methods for improving the gastrointestinal tract health in animals, bacterial isolates and probiotic formulations comprising these isolates are provided herein. The bacterial isolates are *Bacillus* spp. selected from environmental sources that are capable of improving the health of poultry. These isolates were selected for their ability to 1) reduce *Salmonella* or other food-borne bacteria pathogenic to humans, 2) improve production parameters in commercial poultry operations, or 3) reduce enteric poultry bacterial pathogens. No known *Bacillus* DFM product, *Bacillus* isolate, or combination of *Bacillus* isolates are able to accomplish all three tasks.

In one aspect, methods for improving gastrointestinal tract health in animals are provided. The methods include administering an endospore-forming bacterium to an animal. The endospore-forming bacteria are capable of reducing the number or growth of bacterial pathogens in the gastrointestinal tract of the animal. In addition, administration of the endospore-forming bacterium to the animal improves at least one production parameter in the animal.

In another aspect, bacterial isolates selected using the methods disclosed herein are provided and include *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *B. licheniformis* B1 (NRRL Deposit Number B-50907), *B. subtilis* B2 (NRRL Deposit Number B-50908), *B. licheniformis* RW25 (NRRL Deposit Number B-50911), *B. licheniformis* RW32 (NRRL Deposit Number B-50912), and *B. licheniformis* RW41 (NRRL Deposit Number B-50913).

In yet another aspect, multi-isolate combinations and probiotic compositions of the bacterial isolates disclosed herein are provided. In one embodiment, a combination of *B. subtilis* (one or more distinct isolates or strains) and/or *B. licheniformis* (at least one isolate) is provided. The bacterial isolates and probiotic formulations provided here improve upon current technology because they increase performance of commercial poultry, diminish common bacterial pathogens from within the gut of commercial poultry, and reduce common food-borne illness-associated bacteria, such as *Salmonella*, from within the gut of commercial poultry.

In a further aspect, animal feed comprising the probiotic compositions or bacterial isolates disclosed herein is provided. The feed may comprise between about $10^4$ and $10^9$ cfu/gm finished feed.

In still another aspect, methods for improving poultry health are provided. The methods include administration of the probiotic formulation or the animal feed described herein to an animal. The gastrointestinal health of the animal may be improved by the method.

In a still further aspect, methods of selecting bacterial strains for use in probiotic formulations are provided. The methods include selecting facultative anaerobic bacterial strains capable of forming endospores, selecting bacterial strains capable of reducing growth of pathogenic bacteria such as *Salmonella enteritidis, Salmonella typhimurium, Campylobacter jejuni* or *Clostridium perfringens* in mixed cultures in vitro or in the gastrointestinal tract of animals, selecting bacterial strains capable of improving the growth rate of commercial poultry, reducing the severity of necrotic enteritis and/or persisting in the gastrointestinal tract of poultry and removing any selected bacterial strains not considered GRAS (Generally Regarded As Safe) by the Food and Drug Administration (FDA), not eligible for inclusion into animal feed by the Association of American Feed Control Officials (AAFCO) or capable of hemolysis of sheep red blood cells.

BRIEF DESCRIPTION OF THE DRAWINGS

A more complete understanding of the present invention may be derived by referring to the detailed description and claims when considered in connection with the Figures.

FIG. 1 is a diagram of the in vitro portion of the isolate selection procedures used to isolate and select candidate probiotic/DFM isolates.

FIG. 2 is a diagram of the in vivo portion of the isolate selection procedures used to isolate and select candidate probiotic/DFM isolates.

DETAILED DESCRIPTION

Methods, compositions and bacterial isolates for improved gastrointestinal health of poultry are disclosed. The compositions include probiotic formulations or Direct-Fed Microbials (DFM) and animal feed products. Methods of administration to improve animal health and reduce contamination of the human food chain and methods for isolating specific bacterial strains useful in the methods are also disclosed. The methods and compositions provided herein also produce greater consistency of production parameters within a group of animals.

Methods for improving gastrointestinal tract health in animals include administering an endospore-forming bacterium to an animal. The bacteria may be administered as spores, but need not be. The endospore-forming bacteria are capable of reducing the ability of bacterial pathogens to grow in the gastrointestinal tract of the animal. The number of bacterial pathogens found within the gastrointestinal tract reduced in animals administered the endospore-forming bacteria as compared to control animals not administered the bacteria. Bacterial pathogens refers to bacteria capable of causing disease i.e., morbidity or mortality, in either the animal being administered the bacteria or humans. Pathogenic bacteria also include those bacteria capable of causing food-borne illness in humans.

The endospore-forming bacteria can be any bacteria capable of sporulation such as those of the genus *Bacillus*, in particular *Bacillus subtilis* or *Bacillus licheniformis*. The endospore-forming bacteria are suitably not pathogenic, i.e., they are not capable of causing morbidity or mortality in the animals being treated. Suitably the bacteria are facultative anaerobes and capable of replicating and/or persisting within the gastrointestinal tract of the animal. Suitably, the bacteria are Generally Regarded as Safe (GRAS) by the U.S. Food and Drug Administration (FDA) and acceptable for inclusion in an animal diet or water by the Association of American Feed Control Officials (AAFCO). Suitably the endospore-forming bacteria are not capable of causing hemolysis when incubated with or grown on media containing red blood cells. Suitably the endospore-forming bacteria are capable of reducing the growth of at least one pathogenic bacterium.

Administration of the bacteria improves the gastrointestinal health of the animal. The gastrointestinal health includes the prevention of disease of the gastrointestinal tract itself, such as necrotic enteritis of the intestines, or the pathogenic bacterial load of the intestines, ceca or lower intestine and increase in production parameters for the treated animals as compared to controls. Production parameters include but are not limited to average daily weight gain, feed conversion rates, consistency of growth among a group of animals, ability to reproduce and bear healthy offspring, ability to produce eggs or milk and the quantity and quality of such production.

In accordance with one aspect, an exemplary composition or formulation can include one or more bacteria capable of forming endospores. Bacteria capable of forming endospores include bacteria of the genus *Bacillus*. Specific *B. subtilis* and *B. licheniformis* bacterial isolates are disclosed herein, but other endospore forming bacteria suitable for use in the methods and compositions disclosed herein can be isolated and selected by those of skill in the art using the methods of selection described below and in the Examples. For example, a composition can comprise a formulation containing one or two different isolates of *B. subtilis* and/or one or two isolates of *B. licheniformis*, wherein each isolate is independently selected to perform a specific role and/or function. The combination of these isolates can be combined with an agricultural animal feed (specifically poultry feed) and ultimately used to improve the health and productivity of the agricultural animals (e.g. livestock and/or poultry). For example the isolates and/or the combined isolate formulations can reduce pathogenic bacteria, in particular food-borne illness associated bacteria, that cause the eggs or meat to be contaminated, can reduce gut pathogens in the poultry, and increase weight gain or egg production of commercial poultry.

Specifically, the isolates can decrease the occurrence or load of at least one of *Salmonella, Campylobacter* and *Clostridium*. Through the reduction of *C. perfringens* in the gastrointestinal tract of the agricultural animals and through other beneficial reactions of the isolates with the agricultural animals, the occurrence of necrotic enteritis is reduced. In addition, reducing these bacteria decreases the mortality rate of the agricultural animals, and the average daily weight gain of the agricultural animals is increased. In the case of poultry, a reduced level of *Salmonella* within the gastrointestinal tract may lead to less carcass contamination as well as reduce the likelihood of *Salmonella* contaminated eggs.

As described in the examples below, the bacterial isolates were selected for their ability to form spores and as such are resistant to temperature extremes. The selected bacteria are facultative anaerobes and are not hemolytic. The bacteria are capable of inhibiting or reducing the growth of both gram positive and gram negative bacteria such as *Salmonella, Clostridium* and *Campylobacter*. The ability to reduce pathogenic bacterial growth allows the selected bacteria to reduce necrotic enteritis in poultry. The selected bacteria are also capable of increasing the growth rate and gastrointestinal health of commercial poultry and are capable of persisting and colonizing in the gastrointestinal tract of poultry. The isolates are all considered as GRAS (Generally recognized as safe) by the FDA and are eligible for inclusion in animal feed by the AAFCO. Furthermore, these particular isolates are able to go through their entire life cycle within the gastrointestinal tract of agricultural animals, specifically in commercial poultry.

The bacterial isolates identified in the Examples and capable of being used in probiotic formulations or in animal feed for use in the methods described herein are the following: *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *B. licheniformis* B1 (NRRL Deposit Number B-50907), *B. subtilis* B2 (NRRL Deposit Number B-50908), *B. licheniformis* RW25 (NRRL Deposit Number B-50911), *B. licheniformis* RW32 (NRRL Deposit Number B-50912), and *B. licheniformis* RW41 (NRRL Deposit Number B-50913). The bacterial isolates have been deposited with the Agricultural Research Service Culture Collection (NRRL), 1815 North University Street, Peoria, Ill. 61604, U.S.A., under the above-identified accession numbers. The bacterial isolates designated as "*Bacillus subtilis* AM0904", "*Bacillus subtilis* AM0911", "*Bacillus subtilis* NP122", "*Bacillus subtilis* NP119B", "*B. subtilis* B2", "*B. licheniformis* B1", "*B. licheniformis* RW25", "*B. licheniformis* RW32", and "*B. licheniformis* RW41" were mailed by Federal Express to the NRRL by Ross Wolfenden of Pacific Vet Group—USA, Inc. on Mar. 6, 2014.

The spore, or inert, survival form of *Bacillus* spp. do not produce any known effectors which may reduce bacterial pathogens in the gastrointestinal tract or have other beneficial effects on the animal. In contrast, the vegetative form of the bacteria can produce effectors. Thus, reactivation and germination of the spores after administration is likely important to the improvement of poultry gastrointestinal health. The ability of *Bacillus* probiotic products to germinate within the gut of commercial poultry has not been adequately investigated. The bacterial isolates described herein were also selected for their ability to reactivate, germinate and colonize or persist within animals after administration of spores of the bacteria to animals.

Probiotic formulations comprising at least one of the bacterial isolates provided herein are also disclosed. The probiotic formulation may comprise a combination of the bacterial isolates disclosed herein or may include bacterial isolates other than those disclosed herein. Suitably, the bacteria used are capable of forming endospores, are capable of reducing the pathogenic bacterial loads in the gastrointestinal tract and are capable of increasing at least one production parameter. For example, the probiotic formulation may include at least one *Bacillus subtilis* strain and/or at least one *Bacillus licheniformis* strain. In other examples, the probiotic formulation may include two or more *Bacillus subtilis* strains or two or more *Bacillus licheniformis* strains. The bacterial isolates may be used in any combination in the probiotic formulations. For example as combination of NP122 and B2 may be used. Alternatively, NP122 and B2 may be used in combination with AM0904 or AM0911. Any other possible combination of the bacterial isolates provided herein may also be made.

The ratio of one isolate to another in a combination probiotic formulation can vary within a wide range. Suitably the ratio of bacterial isolates is between 0.1:1 and 10:1, suitably between 0.5:1 and 5:1, more suitably 1:1 to 3:1, more suitably it is between 1:1 and 2:1. In one embodiment the ratio of NP122 to B2 to AM0904 was 5:5.1. The ratios are based on the colony forming units (cfu) of the bacterial spores after reactivation.

The probiotic formulation is capable of improving the health of animals after administration to animals. In particular, the probiotic formulation or animal feed comprising the probiotic formulation is capable of improving the gastrointestinal health of poultry. This may include reducing the incidence or severity of necrotic enteritis (by at least 10%, 15% or even 20% as compared to controls and mortality may be prevented), reducing the bacterial load in the intestines of the animal, specifically with regards to levels of at least one of *Salmonella*, *Campylobacter* or *Clostridium perfringens* in the gastrointestinal tract of poultry (at least 50% decrease in recovery, suitably at least 60%, 70%, 80%, 90% or even more of a decrease in recovery as compared to controls), and increasing the daily average weight gain of an animal (at least a 3% increase suitably at least a 5%, 7%, 10%, 20%, 30% 40%, 50%, 55%, 60% or even more increase in weight gain as compared to controls (measured as average daily weight gain)). The feed conversion rate may also be increased as compared to controls. For example the feed conversion rate may be increased by 2%, 3%, 5%, 7%, 10% or more.

Administration of the probiotic formulation may also reduce the level or number of potential bacterial food-borne pathogens of humans in the gastrointestinal tract of commercial poultry. In particular the level of *Salmonella* and *Campylobacter* spp. in the gastrointestinal tract of animals administered the probiotic formulation may be reduced as compared to control animals not administered the probiotic or the spore-forming bacteria. Such a reduction in potential human pathogen load in the gastrointestinal tract of poultry will limit the opportunity of contaminating the human food chain either during preparation of meat for human consumption or via contamination of poultry eggs or milk.

These isolates, probiotic formulations comprising the isolates or animal feed comprising the isolates or combinations thereof may be administered to animals orally. Oral administration includes, but is not limited to, delivery in feed, water, by oral gavage or aerosol spray. Suitably the animal is as poultry, more suitably a chicken or turkey. If supplied in an animal feed, the feed may comprise between $10^4$ and $10^9$ cfu bacteria/gm of finished feed. Suitably the feed comprises between $10^5$ and $5 \times 10^7$ cfu bacteria/gm feed. The probiotic formulation may be added to the feed during production, after production by the supplier or by the person feeding the animals, just prior to providing the food to the animals. The endospore-forming bacteria used in the methods and compositions described herein are particularly suitable because they are capable of surviving (as spores) the heat and pressure conditions of the process of producing a dry pelleted feed product.

These isolates or isolate combinations for inclusion in the methods and including those isolates selected and described in the Examples are selected for inclusion in agricultural animal diets to increase overall gastrointestinal health, improve production performance, and reduce enteric bacterial pathogens of importance to both animal health and human food safety. These isolates alone or in combination may be added to poultry diets at the rate of about $10^4$ to $10^9$ ($1.1 \times 10^7$ in the Examples) spores per gram of finished feed for optimal inclusion rate, if the bacteria or probiotic compositions being administered continuously. A higher inclusion rate may be necessary if spores of the bacteria or the compositions are provided intermittently. While administration though the feed is the primary route of administration, the spores of these isolates may also be administered via the drinking water, through course spray, through aerosol spray, or through any other means by which the agricultural animals may ingest these isolates or combination of isolates.

Methods of isolating bacteria strains for inclusion in probiotic formulations are also provided herein and are depicted in FIGS. 1 and 2. The methods include both in vitro and in vivo tests to select bacteria from a source and may be completed in any order. Sources of potential bacterial isolates include animal feces, environmental or soil samples, laboratory stocks or bacteria from tissue and cell supply warehouses such as the American Type Culture Collection (ATCC). The bacteria may then be isolated and selected by selecting facultative anaerobic bacterial strains capable of forming spores; capable of reducing the growth of or killing *Salmonella enteritidis*, *Salmonella typhimurium*, *Campylobacter jejuni* and/or *Clostridium perfringens*; capable of improving growth rate of commercial poultry; capable of reducing the severity of necrotic enteritis; capable of persisting in the gastrointestinal tract of poultry. The methods also include removing bacterial strains not considered GRAS by the FDA, not eligible for inclusion into animal feed by AAFCO or those capable of hemolysis. Bacterial strains fitting these criteria may then be included in probiotic formulations.

The present invention sets forth exemplary isolates, compositions, and methods for improving GI tract health in animals. It will be understood that the description is of exemplary embodiments of the invention, and that the invention is not limited to the specific forms shown. Various modifications may be made in the design and arrangement of the elements set forth herein without departing from the scope of the invention. For example, the various components can be used in various combinations in addition to those illustrated in the exemplary embodiments, and the various steps can be conducted in different orders. These and other changes or modifications are intended to be included within the scope of the present invention

EXAMPLES

Environmental samples or poultry fecal supplies were collected using sterile cotton swabs and placed into a sterile borosilicate tube for transport. An outline of the in vitro tests used to select bacterial isolates is depicted in FIG. 1. The swabs were either immersed in 50% ethanol or heated to 70° C. for 15 min prior to being used to inoculate tryptic soy agar (TSA) and Spizizen potato agar (SPA) to select for *Bacillus* spp. After incubation for 24 h and 72 h respectively at 37° C., the resulting cultures were overlaid with a TSA soft agar containing novobiocin (NO) at 25 μg/ml and $10^6$ cfu/ml *Salmonella enterica* serovar Enteritidis phage type 13A (SE) originally obtained from the U.S. Department of Agriculture National Veterinary Services Laboratory. After incubation, those colonies which produced zones of inhibition in the SE overlay were selected for isolation. The selected colonies were pasteurized in 50% ethanol for 30 minutes then isolated on the same medium from which they were selected and incubated for either 24 h (TSA) or 72 h (SPA) at 37° C. The isolates ability to inhibit growth of SE was confirmed using a second SE overlay. Those isolates with confirmed in vitro ability to inhibit SE growth were amplified and selected for further analysis.

TSA plates containing sheep blood were inoculated with the isolates and incubated for 24 h at 37° C. The plates were then evaluated and scored for level of hemolysis. All isolates causing alpha or beta hemolysis were not evaluated further. Similarly, further testing of any isolate whose colony morphology was consistent with that of the *B. cereus* group (*B. cereus, B. mycoides, B. thurigensis,* and *B. anthrasis*) was discontinued. Those isolates with the greatest in vivo antimicrobial activity (anti-SE) were identified using the bioMerieux API 50 CHB test kit.

The *Bacillus* isolates identified using the above methods were further screened for in vitro microbial inhibitory activity for *Clostridium perfringens* (CP) and *Campylobacter jejuni*. A similar overlay method as described above was used, but overlays were incubated anaerobically and NO was not added to the overlay media.

In an effort to grow high numbers of viable spores, a solid state fermentation media was used. Only isolates which were able to grow and sporulate to greater than $1\times10^{10}$ spores per gram were selected for further evaluation. Three samples of each of the sporulated candidate cultures were diluted 1:9 in 0.9% sterile saline. Duplicate samples were subjected to room temperature for 30 min or 100° C. for 10 min to assess heat stability of the candidate spores. Following the heat treatments, the spore solutions were diluted, plated and incubated overnight at 37° C. on TSA plates for colony forming unit determination. Only isolates whose spores lost less than 1 $\log_{10}$ unit after heat treatment were further evaluated.

Isolates which passed the in vitro testing were evaluated using as series of in vivo tests illustrated in FIG. 2. These isolates were selected for further analysis in in vivo trials with poults and chicks due to their performance in the in vitro tests. An antibiotic free corn-soy turkey starter diet produced by the University of Arkansas Department of Poultry Science feed mill (Fayetteville, Ark. 72701) and formulated to meet or exceed the National Research Council requirements for critical nutrients of young poults and chicks was used as the basal diet for these experiments. Spores from the candidate isolates were added to the basal diet at a concentration of about $10^6$ cfu/gm of feed and mixed with a rotary mixer for 15 minutes to distribute spores throughout feed.

Commercial broiler chicks and commercial turkeys were obtained on day of hatch and orally gavaged with *Salmonella typhimurium* (ST) at a dose of about $10^5$ cfu/chick. They were then randomly assigned to groups: negative control (basal diet) or a group fed the basal diet containing spores of one of the candidate isolates (n=20/group). The poults and chicks were then tagged, weighed, and placed into the appropriate floor pens by treatment. The poults and chicks had fresh pine shaving as bedding material and had free access to feed and water throughout the duration of the trial. At the conclusion of the trial, on or about day 10, the chicks and poults were weighed. The cecal tonsils were aseptically removed and placed into tetrathionate broth. The ceca were homogenized and diluted 1:4 by weight with sterile saline. Total viable counts of ST were determined by plating dilutions on BGA plates with NO (25 μg/mL) and nalidixic acid (NA; 20 μg/mL) after 24 h of incubation at 37° C. The plates were examined for the presence of colonies typical of this strain of ST on BGA media. Isolates which produced body weight gains greater than control and led to a decreased recovery of ST were selected for further testing, while unsuccessful isolates were discarded.

Successful isolates from the above test were again incorporated in a poultry ration as described above. Spores from the candidate isolates were added to the basal diet and mixed with a rotary mixer for 15 minutes to distribute spores throughout feed. Commercial broiler chicks were obtained on day of hatch and orally gavaged with *Salmonella typhimurium* (ST). They were then randomly assigned to groups: negative control (basal diet) or a group fed the basal diet containing spores of one of the candidate isolates. The chicks were then tagged, weighed, and placed into the appropriate floor pens by treatment group (n=20/group). The chicks had fresh pine shaving as bedding material and had free access to feed and water throughout the duration of the trial. At approximately 3 weeks of the age all chicks were weighed then orally gavaged with *Eimeria maxima* (EM). On days 3-5 post challenge with EM all chicks were challenged with *Clostridium perfringens*. On or about 4 weeks of age all chicks were weighed and the chicks intestines were assigned a subjective score for necrotic enteritis lesions as previously described (Avian Diseases 51(4):834-839 (2007)). Isolates which significantly reduced ($p<0.5$) the severity of necrotic enteritis were kept for further evaluation.

In a subsequent test, all successful isolates were evaluated for their ability to persist within the gastrointestinal tract of commercial poultry. Commercial broiler chicks were obtained on day of hatch them randomly separated into groups. These chicks were placed by group into isolator units. The chicks were fed a standard broiler starter ration which had previously been heat sterilized. On or about day 7, the individual groups (n=20) of broiler chicks were orally gavaged with about $10^9$ cfu of the candidate isolates or sterile saline (as a negative control). The persistence of the candidate isolates was evaluated by enumerating ingesta from individual birds in most experiments. Many of the tested isolates declined in numbers markedly such that by 72 hours post-gavage, cfu of less than $1\times10^3$ cfu/gm ingesta were enumerated, declining similarly to an expected gut passage time of approximately 4-6 hours, indicating that these isolates were not replicating within the gastrointestinal tract. However, some isolates were recovered at levels of greater than $1\times10^5$ cfu/gm at 96 hours post-gavage. Such isolates were selected for further evaluation. Isolates which persisted longer than their predicted half life were selected for continued evaluation.

Using the selection processes a total of nine isolates were found to be potentially useful, alone or in combination with other isolates, as a probiotic or DFM for use in commercial poultry. These nine isolates include *Bacillus subtilis* strains AM0904 (NRRL Deposit Number B-50914), AM0911 (NRRL Deposit Number B-50915), NP122 (NRRL Deposit Number B-50910), NP119B (NRRL Deposit Number B-50909), and B2 (NRRL Deposit Number B-50908) and *B. licheniformis* strains to include B1 (NRRL Deposit Number B-50907), RW25 (NRRL Deposit Number B-50911), RW32 (NRRL Deposit Number B-50912), and RW41 (NRRL Deposit Number B-50913).

In a final series of testing, the isolates were retested not as individual isolates, but in combinations of 2 to 3 isolates. These combinations were subjected to the aforementioned in vivo tests and evaluated using the same parameters stated above, as well as compared to the performance of the individual isolates in these same tests. The best performing isolates and isolate combinations were used further in field testing and were considered as potential candidates for inclusion in a final product.

Combinations of the above listed isolates may include, but are not limited to, the following: NP122, AM0904, and B2. This combination has been shown to be effective when administered in the ratio of 5:5:1 for isolates NP122, B2 and AM0904 respectively. When administered in the feed this combination has been show to be effective to yield significant ($p<0.05$) reduction of *Salmonella* infection (50-90% decrease in recovery), necrotic enteritis mortality and lesions (22% in controls to 0% in treated), and improving body weight gain during challenge periods by more than 50% when administered at the rate of $5\times10^6:5\times10^6:1\times10^6$:spores per gram of finished feed for isolates NP122, B2 and AM0904, respectively.

What is claimed is:

1. A probiotic formulation comprising a bacterial isolate selected from the group of *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *B. licheniformis* B1 (NRRL Deposit Number B-50907), *B. subtilis* B2 (Deposit Number B-50908), *B. licheniformis* RW25 (NRRL Deposit Number B-50911), *B. licheniformis* RW32 (NRRL Deposit Number B-50912), and *B. licheniformis* RW41 (NRRL Deposit Number B-50913), wherein the formulation comprises at least one *Bacillus subtilis* isolate and at least one *Bacillus licheniformis* isolate, or at least two *Bacillus subtilis* isolates.

2. The probiotic formulation of claim 1, wherein the probiotic formulation is capable of improving gastrointestinal tract health in poultry.

3. The probiotic formulation of claim 2, wherein improving the gastrointestinal tract health comprises at least one of reducing potential bacterial food-borne pathogens of humans from the gastrointestinal tract of commercial poultry, reducing at least one of *Salmonella*, *Campylobacter* or *Clostridium perfringens* in the gastrointestinal tract of poultry, or increasing the daily weight gain of the poultry.

4. The probiotic formulation of claim 1, wherein the ratio of one *Bacillus subtilis* isolate and one *Bacillus licheniformis* isolate, or two *Bacillus subtilis* isolates is between 0.5:1 and 3:1 colony forming units (cfu).

5. The probiotic formulation of claim 1, wherein the *Bacillus subtilis* isolates comprise NP122, AM0904 or B2.

6. The probiotic formulation of claim 5, wherein the *Bacillus subtilis* isolates NP122, B2 and AM0904 are present in a ratio of about 5:5:1 colony forming units (cfu).

7. The probiotic formulation of claim 1, wherein the formulation is configured to be administered via an agricultural animal feed substrate.

8. An animal feed comprising the probiotic formulation of claim 1, wherein the feed comprises between $10^4$ and $10^9$ spores/gram finished feed.

9. The probiotic formulation of claim 1, wherein the bacterial isolates are capable of reducing the severity of necrotic enteritis in poultry, and wherein the bacterial isolates are not capable of hemolysis and are considered as Generally Recognized As Safe by the United States Food and Drug Administration.

10. A method for improving gastrointestinal tract health in animals comprising:

administering a probiotic formulation to an animal, comprising a bacterial isolate selected from the group of *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *B. licheniformis* B1 (NRRL Deposit Number B-50907), *B. subtilis* B2 (Deposit Number B-50908), *B. licheniformis* RW25 (NRRL Deposit Number B-50911), *B. licheniformis* RW32 (NRRL Deposit Number B-50912), and *B. licheniformis* RW41 (NRRL Deposit Number B-50913), wherein the formulation comprises at least one *Bacillus subtilis* isolate and at least one *Bacillus licheniformis* isolate, or at least two *Bacillus subtilis* isolates, wherein the bacterial isolates are capable of reducing growth of *Salmonella enteritidis*, *Campylobacter jejuni* and *Clostridium perfringens* in vitro and are capable of reducing the growth of *Salmonella typhimurium* in the gastrointestinal tract of the animal, and wherein the bacterial isolates are capable of persisting in the gastrointestinal tract of poultry for over six hours.

11. The method of claim 10, wherein the probiotic formulation is administered as an endospore comprised within a dry pelleted animal feed.

12. The method of claim 10, wherein the bacterial isolates are capable of reducing the severity of necrotic enteritis in poultry, and wherein the bacterial isolates are not capable of hemolysis and are considered as Generally Recognized As Safe by the United States Food and Drug Administration.

13. The method of claim 10, wherein the probiotic formulation is administered via the animal feed.

14. The method of claim 10, wherein the bacterial isolates are capable of surviving animal feed processing.

15. The method of claim 1, wherein the animals are poultry.

16. The method of claim 10, wherein the probiotic formulation improves at least one production parameter in the animal, wherein the production parameter is selected from increasing the daily weight gain of the animal, or decreasing morbidity or mortality of the animal from bacterial pathogens.

17. A method for improving gastrointestinal tract health in an animal comprising: orally administering a probiotic formulation comprising a bacterial isolate selected from the group of *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *B. licheniformis* B1 (NRRL Deposit Number B-50907), *B. subtilis* B2 (Deposit Number B-50908), *B. licheniformis* RW25 (NRRL Deposit Number B-50911), *B. licheniformis* RW32 (NRRL Deposit Number B-50912), and *B. licheniformis* RW41 (NRRL Deposit Number B-50913), wherein the formulation comprises at least one *Bacillus subtilis* isolate and at least one *Bacillus licheniformis* isolate, or at least two *Bacillus subtilis* isolates to the animal.

18. The method of claim 17, wherein oral administration includes delivery via feed, water, oral gavage, or aerosol spray.

19. The method of claim 17, wherein the animal is poultry.

* * * * *